United States Patent
Schelhaas et al.

(10) Patent No.: US 6,790,976 B2
(45) Date of Patent: Sep. 14, 2004

(54) PROCESS FOR PRODUCING ALIPHATIC TRICARBONITRILES

(75) Inventors: Michael Schelhaas, Köln (DE); Manfred Jautelat, Burscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 474 days.

(21) Appl. No.: 09/893,858

(22) Filed: Jun. 28, 2001

(65) Prior Publication Data

US 2002/0007081 A1 Jan. 17, 2002

(30) Foreign Application Priority Data

Jul. 6, 2000 (DE) .......................................... 100 32 881

(51) Int. Cl.⁷ .......................................... C07C 253/00
(52) U.S. Cl. .................................................... 558/308
(58) Field of Search ........................................ 558/308

(56) References Cited

U.S. PATENT DOCUMENTS

| | | | |
|---|---|---|---|
| 2,307,643 A | 1/1943 | Signaigo | 260/464 |
| 3,375,237 A | 3/1968 | Baizer | 260/88.7 |

FOREIGN PATENT DOCUMENTS

| | | |
|---|---|---|
| DE | 196 37 428 | 3/1998 |
| DE | 196 49 394 | 6/1998 |
| JP | 62-270550 | 11/1987 |
| JP | 5-263012 | 10/1993 |

OTHER PUBLICATIONS

Journal of the Chemical Society (month unavailable) 1909, p. 700, Abstracts of Chemical Papers.
Tsuruda, T,; O'Driscoll, K.F.; eds. Structure & Mechanism in Vinyl Polymerisation; Marcel Dekker; NY (month unavailable) 1969, Chaper 11, pp. 345–448, J. Smid, Elementary Steps in Anionic Vinyl Polymerization.
Database WPI, Section Ch, Week 198801, Derwent Publications Ltd., London, GB; AN 1988–004871, XP002173973, & JP 62 270550 A (Asahi Chem Ind Co Ltd), Nov. 24, 1987.
Database WPI, Section Ch, Week 197902, Derwent Publications Ltd., London, GB; AN 1979–02876B, XP002173974, & JP 53 135926 A (Asahi Chem Ind Co Ltd), Nov. 28, 1978.
Journal of Applied Chemistry of the USSR (month unavailable) 1972, pp. 2683–2684, E. P. Usova et al , "Identification of a High–Boiling Impurity in Adipodinitrile Made From Acrylonitrile".
Journal of the American Chemical Society, Bd. 109, Nr. 4, Feb. 18, 1987, Seiten 1160–1170, XP002173970, DC US, Seite 1166, Zeile 18–Zeile 23, R. M. Coates et al, "Synthesis and Claisen Rearrangement of Alkoxyalkyl Enol Ethers. Evidence for a Dipolar Transition State".
Chemical Abstracts, vol. 101, No. 21, Nov. 19, 1984, Columbus, OH, US: abstract No. 191180v, Seite 702; Spalte 1; XP002173971, Zusammenfassung, & Synthetic Communications, Bd. 14, Nr. 10, (month unavailable), 1984, Seiten 967–972, Marcel Dekker, Inc., Basel, CH ISSN: 0039–7911, L. Rodriguez–Hahn, "A Study of the Thorpe–Zeigler Reaction in Very Mild Conditions.".

*Primary Examiner*—Joseph K. McKane
*Assistant Examiner*—Kamal Saeed
(74) *Attorney, Agent, or Firm*—Joseph C. Gil; Thomas W. Roy; Gary F. Matz

(57) ABSTRACT

The present invention relates to a process for producing tricarbonitriles corresponding to formula I

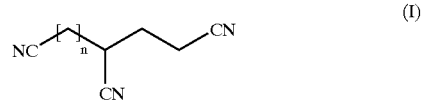

(I)

wherein n is an integer from 2 to 11
by forming an intermediate in the presence of a strong base in a first stage from an aliphatic α-ω-dinitrile corresponding to formula II

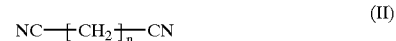

(II)

wherein n is an integer from 3 to 12,
and reacting the intermediate in a second stage to form a trinitrile corresponding to formula I by the addition of acrylonitrile.

7 Claims, No Drawings

PROCESS FOR PRODUCING ALIPHATIC TRICARBONITRILES

BACKGROUND OF THE INVENTION

1. Field of the Invention

The present invention relates to a process for producing aliphatic tricarbonitriles, in particular 1,3,6-hexanetricarbonitrile, in a two-stage synthesis by reacting in a first stage an aliphatic α-ω-dinitrile in the presence of a strong base to form an intermediate, which is reacted in a second stage with acrylonitrile under weakly basic conditions.

2. Description of the Prior Art 1,3,6-hexanetricarbonitrile is an important intermediate for a number of industrially used products. For example tricarboxylic acids, which can be used as detergents, can be obtained by hydrolysis (DE-A-196 37 428). The corresponding hydrogenation of trinitrile leads to 1,3,6-triaminohexane, which can then be reacted in a further stage by phosgenation to form 1,3,6-triisocyanatohexane. This compound is used as an important basic building block in polyurethane (PU) chemistry, for example, for producing polyurethane adhesives or polyurethane coatings.

1,3,6-hexanetricarbonitrile is formed as a by-product during electrochemical production of adiponitrile (JP-A-62270550). The undesirable by-product has to be isolated from the distillation residue in a complex process. Currently, this is the only industrial method of obtaining 1,3,6-hexanetricarbonitrile.

SU-A-194 088 describes the adjustment of the electrochemical synthesis of adiponitrile with an unsaturated intermediate of adiponitrile being used as starting product for producing 1,3,6-hexanetricarbonitrile. However, this intermediate cannot be obtained industrially.

The cyclization of adiponitrile to 2-amino-1-cyclopentene-1-carbonitrile is known (Journal of the Chemical Society 1909, 700). The reaction is carried out under strongly basic reaction conditions, i.e. bases such as alkali hydrides, alkali amides or alkali-t-butylates are used.

The production of 1,3,6-hexanetricarbonitrile from 2-amino-1-cyclopentene-1-carbonitrile and acrylonitrile in the presence of elemental sodium is also known (Journal of Applied Chemistry of the USSR, 1972, 2683–2684). The use of elemental sodium and the increased safety risk associated therewith rules out transfer to a large scale industrial process.

It has been found that a direct reaction of adiponitrile with acrylonitrile leads to a poorly selective reaction as the deprotonized intermediate can lead to dimerizations and polymerization (Tsuruda, T.; O'Driscoll, K. F.; Eds. Structure and Mechanism in Vinyl Polymerisation; Marcel Dekker: New York, 1969; Chapter 11, p. 345 ff).

An object of the present invention is to provide a process for the selective synthesis of tricarbonitriles, in particular 1,3,6-hexanetricarbonitrile, starting from conventional and readily available starting products and controllable reaction conditions.

This object may be achieved in accordance with the present invention by conducting the reaction in two stages. In a first reaction stage an intermediate is obtained via an aliphatic α-ω-dinitrile under strongly basic conditions; the intermediate is then cyanoethylized selectively while opening the ring with acrylonitrile. Undesirable secondary reactions of the acrylonitile are not observed.

SUMMARY OF THE INVENTION

The present invention relates to a process for producing tricarbonitriles corresponding to formula I

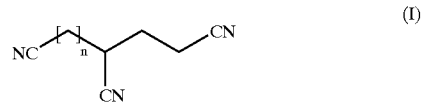

wherein n is an integer from 2 to 11
by forming an intermediate in the presence of a strong base in a first stage from an aliphatic α-ω-dinitrile corresponding to formula II

wherein n is an integer from 3 to 12,
and reacting the intermediate in a second stage to form a trinitrile corresponding to formula I by the addition of acrylonitrile.

DETAILED DESCRIPTION OF THE INVENTION

In a preferred embodiment of the process according to the invention an intermediate is obtained in the first stage from adiponitrile under strongly basic reaction conditions, and is then reacted with acrylonitrile in a second stage to form 1,3,6-hexanetricarbonitrile. The synthesis is preferably carried out as a one pot reaction.

The intermediate can optionally be isolated in the process according to the invention and then reacted with acrylonitrile to form a trinitrile corresponding to formula I.

The intermediate can be identified, for example, as shown by the evaluation of the analytical data, as 2-amino-1-cyclopentene-1-carbonitrile corresponding to formula III

in which n is an integer from 1 to 10.

The first stage of the process according to the invention is carried out at a temperature of 70 to 120° C., preferably 80 to 100° C.

Suitable strong bases include alkali metals, hydrides, amides or alkoxides such as alkali-tert-butylates; potassium-tert-butylate is preferred. Metal oxides and hydroxides of the first and second main group of the periodic table have adequate basicity in complexing solvents such as polyethylene glycols, preferably diglymes, ethyleneglycol dimethylether or polyethyleneglycol dimethylether M 500 (Aldrich), or phase-transfer catalyzed systems, preferably heat-stable phase-transfer catalysts, more preferably Aliquat 175 or Aliquat 336 (Cognis) or Aliplex 186BD (Cognis).

The strong base used in the process according to the invention is added in an amount of 0.5 to 2, preferably from 1 to 1.5 equivalents, based on the α-ω-dinitrile.

After reaction of the α-ω-dinitrile to form the intermediate, acrylonitrile is added with lower basicity of the reaction medium than in the first stage. Preferably, before the addition of acrylonitrile, an equimolar amount of water is added.

The second stage of the synthesis is carried out at a temperature range of 0 to 120° C., preferably 10 to 70° C.

If the intermediate of formula III is optionally isolated, it can be cyanoethylized to form 1,3,6-hexanetricarbonitrile (corresponding to formula I) in a separate second stage with acrylonitrile and with addition of a weak base. 1 to 1.5 equivalents of acrylonitrile based on the molar amount of isolated intermediate corresponding to formula III is added to the reaction.

Suitable weak bases include potassium carbonate, sodium carbonate, sodium phosphate, sodium hydroxide or potassium hydroxide or systems controlled by phase-transfer catalysts such as quaternary ammonium, phosphonium and other onium compounds or crown ether and cryptands. A quaternary ammonium salt (Aliquat 336) in aqueous sodium hydroxide solution is preferably used as a phase-transfer catalyst.

Suitable reaction media for the process according to the invention include inert organic solvents such as benzene, toluene or petroleum ether, preferably toluene.

The process according to the invention can be carried out under an inert atmosphere or in the presence of oxygen and at a pressure of 1 to 50 bar, preferably at atmospheric pressure. The treatment of the dinitrile with bases is advantageously carried out under inert conditions.

Further working up of the tricarbonitrile produced according to the invention is carried out by standard methods known to the person skilled in the art.

EXAMPLES

The stated selectivities describe the ratio of product to conversion. In examples 1 to 4 unreacted intermediates can be worked up in a further stage and re-added to the reaction.

Example 1

One Pot Synthesis for Producing 1,3,6-hexanetricarbonitrile

A mixture of 2.16 g (20 mmol) of adiponitrile, 1.8 g (32 mmol) of KOH powder and 200 mg (0.59 mmol) of tetrabutyl ammonium hydrogen sulphate in 50 ml of toluene were heated to 100° C. under argon for a reaction period of 2 hours. After cooling to room temperature (RT) 1.17 g (22 mmol) of acrylonitrile were added to 10 ml of toluene and the mixture stirred at RT for 2 hours. After adding water the organic phase was separated off and dried, the solvent was distilled off and the residue was examined by gas chromatography.

Trimer yield: 17%
Selectivity with respect to trimers: 40%

Example 2

One Pot Synthesis for Producing 1,3,6-hexanetricarbonitrile 5.41 g (50 mmol) of adiponitrile were added to a suspension of 5.6 g (50 mmol) of potassium-tert.-butylate in 50 ml of toluene under argon and the mixture was heated for 1 hour with reflux. After the mixture was cooled to room temperature 4 ml (60 mmol) of acrylonitrile were slowly added. The mixture was subsequently stirred for 1 hour at RT and diluted with water. The phases were separated, the aqueous phase was extracted with ethyl actetate, the combined organic phases were dried, the solvent was distilled off and the residue was examined by gas chromatography.

Trimer yield: 9.3%
Selectivity with respect to trimers: 18%

Example 3

One Pot Synthesis for Producing 1,3,6-hexanetricarbonitrile 5.41 g (50 mmol) of adiponitrile were added at 65° C. to a suspension of 5.6 g (50 mmol) of potassium-tert.-butylate in 50 ml of toluene under argon and the mixture was heated for 1 hour with reflux. After the mixture was cooled to room temperature 0.9 ml (50 mmol) of water were added and then 4 ml (60 mmol) of acrylonitrile were added slowly. The mixture was subsequently stirred for 1 hour at RT and diluted with water. The phases were separated, the aqueous phase was extracted with ethyl acetate, the combined organic phases were dried, the solvent was distilled off and the residue was examined by gas chromatography.

Trimer yield: 35%
Selectivity with respect to trimers: 47%

Example 4

One Pot Synthesis for Producing 1,3,6-hexanetricarbonitrile 5.41 g (50 mmol) of adiponitrile were added at 65° C. to a suspension of 5.6 g (50 mmol) of potassium-tert.-butylate in 50 ml of toluene under argon and the mixture was heated for 1 hour with reflux. After the mixture was cooled to room temperature 0.9 ml (50 mmol) of water were added and then 4 ml (60 mmol) of acrylonitrile dissolved in 20 ml of toluene were slowly added. The mixture was subsequently stirred for 1 hour at RT and diluted with water. The phases were separated, the aqueous phase was extracted with ethyl acetate, the combined organic phases were dried, the solvent was distilled off and the residue was examined by gas chromatography.

Trimer yield: 43%
Selectivity with respect to trimers: 69%

Example 5

Production of 1,3,6-hexanetricarbonitrile by Isolating 2-amino-1-cyclopentene-1-carbonitrile 216 mg (2 mmol) of adiponitrile and 128 mg (3.2 mmol) of sodium hydroxide micropills were heated for 22 hours to 95° C. in 5 ml of polyethylene glycol dimethyl ether (M 500, Aldrich) as solubilizer. 3 ml of water were added and extracted with toluene. 2-amino-1-cyclopentene-1-carbonitrile yield: 84%

Analysis by NMR Spectroscopy:

$^1$H-NMR (400 MHz, d$^6$-DMSO):
δ (ppm): 1.7–1.8 (m, 2H); 2.3–2.4 (m, 4H); 6.4 (s, br, 2H).
$^{13}$C-NMR (100 MHz, d$^6$-DMSO):
δ (ppm): 22.0; 31.2; 34.2; 68.3; 120.3; 164.4.

583 mg (11 mmol) of acrylonitrile were added at room temperature to a mixture of 1.08 g (10 mmol) of 2-amino-1-cyclopentene-1-carbonitrile, 2 ml of 45% sodium hydroxide solution, 100 mg of Aliquat 336 (Cognis) and 6 ml of toluene and stirred at room temperature for 22 hours. The mixture was diluted with water, the phases were separated, the organic phase was dried, the solvent was distilled off and the residue was examined by gas chromatography.

Trimer yield: 63.2%
Selectivity with respect to trimers: 75%

Example 6

Production of 1,3,6-hexanetricarbonitrile by Isolating 2-amino-1-cyclopentene-1-carbonitrile 583 mg (11 mmol) of acrylonitrile were added at room temperature to a mixture of 1.08 g (10 mmol) of 2-amino-1-cyclopentene-1-carbonitrile (from Example 5), 2 ml (33.7 mmol) of 45% sodium hydroxide solution, 100 mg of Aliquat 336 and 6 ml of toluene and stirred at 50° C. for 22 hours. The mixture was diluted with water, the phases were separated, the organic phase was dried, the solvent was distilled off and the residue was examined by gas chromatography.

Trimer yield: 66.9%
Selectivity with respect to trimers: 79%

Example 7

Production of 1,3,6-hexanetricarbonitrile by Isolating 2-amino-1-cyclopentene-1-carbonitrile A mixture of 32 mg (0.3 mmol) of 2-amino-1-cyclopentene-1-carbonitrile (from Example 5), 3 ml (48 mmol) of 45% sodium hydroxide solution, 0.5 mg (0.0015 mmol) of tetrabutylammonium hydrogen sulphate and 16 mg (0.3 mmol) of acrylonitrile in 7 ml of toluene was heated to 50° C. for 2 hours. After cooling, the toluene phase was examined by gas chromatography.

Trimer yield: 8%

Selectivity with respect to trimers: 90%

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing a tricarbonitrile corresponding to formula I

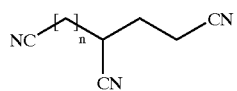
(I)

wherein n is an integer from 2 to 11,
which comprises forming a 2-amino-1-cycloalkene-1-carbonitrile intermediate in a first stage in the presence of a strong base from an aliphatic α-ω-dinitrile corresponding to formula II,

(II)

wherein n is an integer from 3 to 12 and the intermediate has from 4 to 13 carbon atoms in the cycloalkene ring, and reacting the intermediate in a second stage to form a trinitrile corresponding to formula I by the addition of acrylonitrile.

2. The process of claim 1 wherein said aliphatic α-ω-dinitrile comprises adiponitrile.

3. The process of claim 1 wherein the synthesis is carried out as a one pot reaction.

4. The process of claim 1 wherein the strong base is added in an amount of 0.5 to 2 equivalents, based on the α-ω-dinitrile.

5. The process of claim 1 wherein the strong base is added in an amount of 1 to 1.5 equivalents, based on the α-ω-dinitrile.

6. The process of claim 1 wherein the first reaction stage is carried out at a temperature of 70 to 120° C.

7. The process of claim 1 wherein the second reaction stage is carried out at a temperature of 0 to 120° C.

* * * * *